(12) United States Patent
Khalaf Ali et al.

(10) Patent No.: US 11,844,781 B1
(45) Date of Patent: Dec. 19, 2023

(54) POLYMERIC CLOTRIMAZOLE BIOFILM FOR THE TREATMENT OF OTOMYCOSIS

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Ahmed Mohammed Abu-Dief Mohammed, Al-Madina Al-Mounawara (SA); Amr Embaby Elsayed Karamany, Assuit (EG); Mahmoud Ibrahim Mahmoud Abdelmagid, Assuit (EG); Mohammed Sherif Saddik Ibrahim, Sohag (EG); Ali Khames Abd Eltwab Morsy, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/221,183

(22) Filed: Jul. 12, 2023

Related U.S. Application Data

(62) Division of application No. 18/165,085, filed on Feb. 6, 2023.

(51) Int. Cl.
| | |
|---|---|
| *A61K 31/4174* | (2006.01) |
| *A61P 27/16* | (2006.01) |
| *A61P 31/10* | (2006.01) |
| *A61K 9/46* | (2006.01) |
| *A61K 47/10* | (2017.01) |
| *A61K 47/38* | (2006.01) |
| *A61K 9/70* | (2006.01) |
| *A61K 9/00* | (2006.01) |

(52) U.S. Cl.
CPC ........ *A61K 31/4174* (2013.01); *A61K 9/0046* (2013.01); *A61K 9/7007* (2013.01); *A61K 47/10* (2013.01); *A61K 47/38* (2013.01); *A61P 27/16* (2018.01); *A61P 31/10* (2018.01)

(58) Field of Classification Search
CPC .............. A61K 31/4174; A61K 9/0046; A61K 9/7007; A61K 47/10; A61K 47/38; A61P 27/16; A61P 31/10
See application file for complete search history.

(56) References Cited

U.S. PATENT DOCUMENTS

| | | |
|---|---|---|
| 5,346,692 A | 9/1994 | Wohlrab et al. |
| 2015/0297588 A1* | 10/2015 | Branch ................ A61K 9/0046 514/171 |
| 2021/0015770 A1* | 1/2021 | Fedorchak ............. A61K 47/32 |

FOREIGN PATENT DOCUMENTS

| | | |
|---|---|---|
| IN | 201721010423 A | 10/2018 |
| WO | 2022047042 A1 | 3/2022 |

OTHER PUBLICATIONS

Birsan et al., "Development of Dermal Films Containing Miconazole Nitrate," Molecules 2018, 23, 1640. (Year: 2018).*
Ashok et al., "Design and Development of Hydroxypropylmethyl Cellulose (HPMC) Based Polymeric Films of Methotrexate: Physiochemical and Pharmacokinetic Evaluations," The Pharmaceutical Society of Japan (2008). (Year: 2008).*
Singh et al., "Formulation and characterization of transdermal patches for controlled delivery of duloxetine hydrochloride," Journal of Analytical Science and Technology (2016) 7;25. (Year: 2016).*
Abou-halawa et al., "Otomycosis with Perforated Tympanic Membrane: Self medication with Topical Antifungal Solution versus Medicated Ear Wick," Int J Health Sci (Qassim). 6(1): 73-77, Jan. 2012.

* cited by examiner

*Primary Examiner* — Jared Barsky
(74) *Attorney, Agent, or Firm* — Nath, Goldberg & Meyer; Richard C. Litman

(57) ABSTRACT

The polymeric clotrimazole biofilm for the treatment of otomycosis contains clotrimazole or a pharmaceutically acceptable salt thereof as the active pharmaceutical ingredient in a polymer biofilm thug delivery vehicle. The polymer may be a bio compatible polymer, such as hydroxypropylmethylcellulose (HPMC). Propylene glycol may be added to the mixture as a plasticizer to promote formation of the film. The drug and the polymer may be solvated in a casting solvent and then mixed in a 1:3 ratio of drug:polymer. About 15% propylene glycol may be added to the mixture, which is then heated at 40° C. until a thin, flexible film forms. A round, knife-thick patch of the biofilm may be applied to the patient's ear through the external canal and over the tympanic membrane.

5 Claims, No Drawings

POLYMERIC CLOTRIMAZOLE BIOFILM FOR THE TREATMENT OF OTOMYCOSIS

CROSS-REFERENCE TO RELATED APPLICATION

This application is a divisional of U.S. patent application Ser. No. 18/165,085, filed on Feb. 6, 2023, the contents of which are hereby incorporated by reference in their entirety.

BACKGROUND

1. FIELD

The disclosure of the present patent application relates to treatment of perforated tympanic membranes, and particularly to a polymeric clotrimazole biofilm for the treatment of otomycosis, and especially an acute tympanic membrane perforation caused by otomycosis.

2. DESCRIPTION OF THE RELATED ART

Otomycosis is a fungal infection of the ear. It is a common infection in tropical countries, and also occurs in patients who are immunocompromised, or who have overused antibiotics for the treatment of bacterial infections of the ear, thereby killing bacteria that would otherwise controlled the fungus. Patients with otomycosis commonly complain of itching, pain, and often some degree of hearing loss. In some cases, patients experience discharges in the ear, and in more severe cases, otomycosis may cause perforation of the tympanic brane.

Although there are over sixty species of fungus that can cause otomycosis, the two species most commonly at fault are aspergillus and candida. Treatment often takes the form of cleaning the ear, together with ear drops or cream containing a 1% solution of clotrimazole. Such conservative treatment is frequently successful in clearing immediate symptoms, although a recurrence of infection is not uncommon. When the symptoms are severe enough to include perforation of the tympanic membrane, such conservative treatment may result in spontaneous healing of the membrane. However, if symptoms persist, the only option is surgery, and even then some degree of permanent hearing loss may result. It is believed that an alternative drug delivery system that can keep the active pharmaceutical ingredient in the ear in an effective dosage for a longer period of time than ear drops or creams may offer an alternative to surgery and a better prognosis for avoiding permanent hearing loss. Thus, a polymeric clotrimazole biofilm for the treatment of otomycosis solving the aforementioned problems is desired.

SUMMARY

The polymeric clotrimazole biofilm for the treatment of otomycosis contains clotrimazole or a pharmaceutically acceptable salt thereof as the active pharmaceutical ingredient in a polymer biofilm drug delivery vehicle. The polymer may be a biocompatible polymer, such as hydroxypropylmethylcellulose (HPMC). Propylene glycol may be added to the mixture as a plasticizer to promote formation of the film. The drug and the polymer may be solvated in a casting solvent and then mixed in a 1:3 ratio of drug:polymer. About 15% propylene glycol ay be added to the mixture, which is then heated at 40° C. until a thin, flexible film forms. A round, knife-thick patch of the biofilm may be applied to the patient's ear through the external canal and over the tympanic membrane.

These and other features of the present subject matter will become readily apparent upon further review of the following specification.

DETAILED DESCRIPTION OF THE PREFERRED EMBODIMENTS

The polymeric clotrimazole biofilm for the treatment of otomycosis contains clotrimazole or pharmaceutically acceptable salt thereof as the active pharmaceutical ingredient in a polymer biofilm drug delivery vehicle. The polymer may be a biocompatible polymer, such as hydroxypropylmethylcellulose (HPMC). Propylene glycol may be added to the mixture as a plasticizer to promote formation of the film. The drug and the polymer may be solvated in a casting solvent and then mixed in a 1:3 ratio of drug:polymer. About 15% propylene glycol may be added to the mixture, which is then heated at 40° C. until a thin, flexible film forms. A round, knife-thick patch of the biofilm may be applied to the patient's ear through the external canal and over the tympanic membrane.

For otomycosis, particularly where there has been perforation of the tympanic membrane, the success of treatment depends not only on the correct choice of the active component, but also on the form of the drug, as well as its method of application. The major objective of the present treatment is to provide a locally higher effective concentration of the drug, away from metabolism and elimination by blood. Herein, the clotrimazole biofilm releases a controlled amount of clotrimazole, and makes the drug concentration at the infection area always high to prevent fungal regrowth.

Clotrimazole was homogenously dispersed in the polymeric film component and successfully applied for the treatment of acute tympanic membrane perforation caused by otomycosis. In order to treat patients with otomycosis, clotrimazole is often used, which has anti-mycotic and antibacterial pharmacological action. Fungal infection is highly resistant and may relapse a short time after treatment, so the drug must be available at the site of infection in high effective concentration, away from metabolism and elimination by blood. Here, our clotrimazole biofilm formula releases a controlled amount of clotrimazole, and makes the drug concentration at the infection area is always high (decreased antifungal concentration permits fungal regrowth). The success of treatment depends not only on the correct choice of the active component, but also on the form of the drug, as well its method of introduction. Our formulation of clotrimazole biosoluble polymeric films was used to treat otomycosis and tried for healing of tympanic membrane perforation caused by fungi.

The polymeric clotrimazole biofilm for the treatment of otomycosis will be better understood by reference to the following examples.

Example 1

Synthesis of the Biofilm

A polymeric film of clotrimazole was prepared by solvent evaporation technique using hydroxypropylmethylcellulose (HPMC) as the polymer, keeping drug concentration constant (10 mg of clotrimazole/1.0 cm$^2$). The drug: polymer ratio used was (1:3). The required amount of drug and polymer were dispersed separately in casting solvent (ethanol: distilled water in 8.2 ratio). The polymeric dispersions were sonicated for 2 minutes to remove entrapped air bubbles. The two preparations were then mixed, and 15% propylene glycol was incorporated as a plasticizer. This polymeric dispersion of the drug was poured into Teflon plates and allowed to dry in the oven at 40° C. until a flexible film was formed. Dried films were carefully removed and checked for any imperfection or air bubbles. To prevent fast evaporation from the patches, a funnel was placed inverted on the plate.

After ensuring the complete evaporation of the solvent, patches of 9 cm$^2$ were cut with a borer and packed in aluminum foil, and stored in a desiccator to maintain the integrity and elasticity of the films.

Example 2

Method of Treating Otomycosis With the Biofilm

The patches of polymeric film (the clotrimazole films prepared as described in Example 1) were used in treatment of acute tympanic membrane perforation caused by otomycosis under local anesthesia by applying the round knife (a round patch of knife-edge thickness) through the external canal over the tympanic membrane. The result of such treatment was relief from the fungal infection and healing of the perforated tympanic membrane without surgery.

It is to be understood that the polymeric clotrimazole biofilm for the treatment of otomycosis is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating a patient afflicted with otomycosis in at least one ear, comprising applying a patch of a polymer biofilm through the external canal and over the tympanic membrane of the at least one ear, wherein the polymeric biofilm comprises:
   a biocompatible polymer matrix comprising hydroxypropylmethylcellulose (HPMC);
   a pharmaceutically active ingredient for treatment of fungal infections mixed with and uniformly dispersed in the polymer matrix wherein said active ingredient is clotrimazole or a pharmaceutically acceptable salt thereof; and
   a plasticizer added to the mixture of the biocompatible polymer matrix and the pharmaceutically active ingredient, the plasticizer formulating the mixture as a biofilm configured to be applied through an external canal of an ear of a patient infected by otomycosis over a tympanic membrane of the ear for treatment thereof,
   wherein said pharmaceutically active ingredient and said biocompatible polymer matrix are present in the mixture in a ratio of 1:3 pharmaceutically active ingredient: biocompatible polymer matrix; and
   wherein said clotrimazole and said biocompatible polymer are present in the mixture in a ratio of 10 mg clotrimazole/1.0 cm$^2$ polymer matrix.

2. A method of treating a patient afflicted with otomycosis in at least one ear, comprising applying a patch of a polymer biofilm through the external canal and over the tympanic membrane of the at least one ear, wherein the polymeric biofilm consists of:
   a biocompatible polymer matrix comprising hydroxypropylmethylcellulose (HPMC);
   a pharmaceutically active ingredient for treatment of fungal infections mixed with and uniformly dispersed in the polymer matrix wherein said active ingredient is clotrimazole or a pharmaceutically acceptable salt thereof; and
   a plasticizer added to the mixture of the biocompatible polymer matrix and the pharmaceutically active ingredient, the plasticizer formulating the mixture as a biofilm configured to be applied through an external canal of an ear of a patient infected by otomycosis over a tympanic membrane of the ear for treatment thereof,
   wherein said pharmaceutically active ingredient and said biocompatible polymer matrix are present in the mixture in a ratio of 1:3 pharmaceutically active ingredient: biocompatible polymer matrix; and
   wherein said clotrimazole and said biocompatible polymer are present in the mixture in a ratio of 10 mg clotrimazole/1.0 cm$^2$ polymer matrix.

3. A method of treating a patient having an otomycosis in at least one ear, the method comprising applying a polymer biofilm through the external canal and over the tympanic membrane of the at least one ear, wherein the polymeric biofilm comprising:
   a biocompatible polymer matrix comprising hydroxypropylmethylcellulose (HPMC);
   a pharmaceutically active ingredient for treatment of fungal infections mixed with and uniformly dispersed in the polymer matrix wherein said active ingredient is clotrimazole or a pharmaceutically acceptable salt thereof; and
   a plasticizer added to the mixture of the biocompatible polymer matrix and the pharmaceutically active ingredient, the plasticizer formulating the mixture as a biofilm configured to be applied through an external canal of an ear of a patient infected by otomycosis over a tympanic membrane of the ear for treatment thereof,
   wherein said pharmaceutically active ingredient and said biocompatible polymer matrix are present in the mixture in a ratio of 1:3 pharmaceutically active ingredient: biocompatible polymer matrix; and
   wherein said clotrimazole and said biocompatible polymer are present in the mixture in a ratio of 10 mg clotrimazole/1.0 cm$^2$ polymer matrix.

4. The method according to claim 3, wherein said plasticizer comprises propylene glycol.

5. The method according to claim 2, wherein said plasticizer comprises propylene glycol.

* * * * *